(12) United States Patent
Johns et al.

(10) Patent No.: US 8,440,245 B2
(45) Date of Patent: May 14, 2013

(54) METHODS FOR MAKING NUTRITIONAL COMPOSITIONS COMPRISING CURCUMINOIDS

(75) Inventors: Paul W. Johns, Columbus, OH (US); Terrence B. Mazer, New Albany, OH (US)

(73) Assignee: Abbott Laboratories, Abbott Park, IL (US)

(*) Notice: Subject to any disclaimer, the term of this patent is extended or adjusted under 35 U.S.C. 154(b) by 320 days.

(21) Appl. No.: 12/732,686

(22) Filed: Mar. 26, 2010

(65) Prior Publication Data

US 2010/0247734 A1    Sep. 30, 2010

Related U.S. Application Data

(60) Provisional application No. 61/163,683, filed on Mar. 26, 2009.

(51) Int. Cl.
*A23L 1/27* (2006.01)

(52) U.S. Cl.
USPC .......................................... 426/429; 424/758

(58) Field of Classification Search .................. 426/601, 426/429; 424/758
See application file for complete search history.

(56) References Cited

U.S. PATENT DOCUMENTS

| | | | |
|---|---|---|---|
| 4,316,917 A | | 2/1982 | Antoshkiw et al. |
| 5,834,026 A * | | 11/1998 | Lu ................................. 424/498 |
| 5,861,415 A * | | 1/1999 | Majeed et al. ................ 514/321 |
| 5,891,924 A | | 4/1999 | Aggarwal |
| 6,497,908 B1 * | | 12/2002 | Oshiro .......................... 426/238 |
| 6,653,327 B2 | | 11/2003 | Majeed et al. |
| 6,858,247 B2 * | | 2/2005 | Sakai et al. ................... 426/611 |
| 2007/0231371 A1 * | | 10/2007 | Pan et al. ...................... 424/442 |
| 2010/0227828 A1 * | | 9/2010 | Gokaraju et al. ............. 514/27 |

FOREIGN PATENT DOCUMENTS

| | | |
|---|---|---|
| CN | 101589808 A | 12/2009 |
| EP | 0673648 B1 | 11/1998 |
| WO | 2010/111070 | 9/2010 |

OTHER PUBLICATIONS

Tonnesen, H. 1989. Zeitschrift Fur Lebensmitteluntersuchung Und-Forschung A 189(2)116-118.*
Anand, Bioavailability of Curcumin: Problems and Promises, Molecular Pharmaceutics, 2007, 807-818, vol. 4 No. 6.
Sahu, Fluorescence Study of the Curcumin—Casein Micelle Complexation and its Application as a Drug Nanocarrier to Cancer Cells, Biomacromolecules, 2008, 2905-2912, vol. 9.
Began, et al, Interaction of Curcumin with Phosphatidylcholine: A Spectrofluorometric Study, J. Agri. Food Chem., 1999, 4992-4997, vol. 47.
Leung, et al, Encapsulation of Curcumin in Cationic Micelles Suppresses Alkaline Hydrolysis, Langmuir, 2008, 5672-5675, vol. 24.
International Search Report and Written Opinion from PCT/US2010/027477, dated Jul. 27, 2010.
Lin, et al., "Stability and characterization of phospholipid-based curcumin-encapsulated microemulsions," Food Chemistry 2009, vol. 116, p. 923.
Cui, et al., "Enhancement of oral absorption of curcumin by self-microemulsifying drug delivery systems," International Journal of Pharmaceutics 2008, vol. 371, p. 148-155.
Wang, et al., "Enhancing anti-inflammation activity of curcumin through O/W nanoemulsions," Food Chemistry 2008, vol. 108, p. 419.
Aziz, et al., "Solubility of core materials in aqueous polymeric solution effect on microencapsulation of curcumin," US National Library of Medicine, Database Accession No. NLM18058323; XP002588526, 2007.
International Preliminary Report on Patentability from PCT/US2010/027477, dated Jul. 13, 2011.
International Preliminary Report on Patentability for PCT/US2010/27477 dated Sep. 26, 2011.
Office Action from U.S. Appl. No. 12/732,607 dated Sep. 26, 2012.
Office Action from Chinese Application No. 201080022692.x dated Aug. 29, 2012.
Marten et al., "Medium-chain triglycerides," International Dairy Journal 16 (2006), pp. 1374-1382.
Tonnesen, Hanne et al., "Studies of Curcumin and Curcuminoids XVII. Variation in the Content of Curcuminoids in Curcuma Inga L. from Nepal during one Season," Zeitschrift fur Lebensmitteluntersuchung Und-Forschung A, vol. 189 (2), pp. 116-118 (1989).
Whitehurst, "Appendix I, Hydrophile lipophyle balance," Emulsifiers in Food Technology, Blackwell Publishing Ltd., 2004.
Keliang, Nong et al., "Study on Easy Extraction and Column Chromatography Separation of Tumeric Pigments", Technology & Development of Chemical Industry, vol. 35(2), pp. 3-5, Feb. 28, 2006.
Zhaojin, Liu, "Function of Curcumin in the Nutrition and Physiology," Journal of Anhui Agricultural Sciences, vol. 34(7), pp. 1287-1288 and 1291, Jan. 2006.

* cited by examiner

*Primary Examiner* — Carolyn Paden

(57) ABSTRACT

Disclosed are nutritional compositions and methods for preparing the compositions, comprising fat, protein, and carbohydrate, including a combination of curcumin, demethoxycurcumin, and bisdemethoxycurcumin, which combination is solubilized in a polar oil having an HLB value of from about 0.7 to about 14 wherein the weight ratio of the bisdemethoxycurcumin to the curcumin is from about 1:1 to about 1:7 and the weight ratio of the bisdemethoxycurcumin to the demethoxycurcumin is from about 1:1 to about 1:2.5. The composition provides a selected ratio of curcuminoids having improved biological activity, bioavailability, and reduced color impact.

10 Claims, No Drawings

METHODS FOR MAKING NUTRITIONAL COMPOSITIONS COMPRISING CURCUMINOIDS

This application claims the benefit of U.S. Provisional Application No. 61/163,683 filed Mar. 26, 2009

TECHNICAL FIELD

The present disclosure relates to nutritional compositions, and methods of making those compositions, comprising a combination of curcuminoids and a polar oil.

BACKGROUND

Curcuminoids have been studied over the years for a variety of medical and nutritional applications. Many of these studies suggest curcuminoids may have significant anti-oxidant and anti-inflammatory properties and may even inhibit the growth of certain types of cancers.

Curcuminoids such as curcumin, demethoxycurcumin (DSMC) and bis-demethoxycurcumin (BMC) are polyphenols commonly found in Turmeric, a well known and often used spice derived from rhizome of the herb Curcuma longa Linn. These curcuminoids give Turmeric its bright yellow color and are often added in small amounts to various nutritional or foods to add color.

There has been considerable effort over the years to formulate nutritional products comprising curcuminoids at concentrations sufficiently high to provide the consumer with health benefits associated with these natural extracts. There are, however, several characteristics of curcuminoids that make their formulation into such products problematic. Curcuminoids generally have poor bioavailability when taken orally, and thus when formulated at higher concentrations to counter their inherent poor bioavailability to achieve the desired systemic delivery, the products often take on an intense yellow color. This is especially noticeable in aqueous emulsions and other liquid nutritional products.

Moreover, the solubility profile of curcuminoids makes formulation into nutritional products, especially nutritional products in the form of aqueous emulsions or liquids, much more difficult. Curcuminoids have poor solubility in aqueous systems within the acidic to neutral pH range, a pH range that is common for many nutritional liquids or emulsions Curcuminoids are soluble in carriers such as dimethyl sulfoxide, acetone and ethanol, but are poorly soluble in water as well as many types of edible lipids commonly used in the formulation of aqueous nutritional emulsions.

Accordingly, there is a need for aqueous and other nutritional compositions, and methods for preparing these compositions, comprising curcuminoids in an orally acceptable vehicle that delivers the desired bioavailability and bioactivity while minimizing the impact of the curcuminoids on product color.

SUMMARY OF THE DISCLOSURE

One embodiment is directed to a composition comprising fat, protein, and carbohydrate, including a combination of curcumin, demethoxycurcumin, and bisdemethoxycurcumin, which combination is solubilized in a polar oil having an HLB value of from about 0.7 to about 14, wherein the weight ratio of the bisdemethoxycurcumin to the curcumin is from about 1:1 to about 1:7 and the weight ratio of the bisdemethoxycurcumin to the demethoxycurcumin is from about 1:1 to about 1:2.5.

Another embodiment is directed to a composition comprising fat, protein, and carbohydrate in the form of an aqueous emulsion, wherein the aqueous emulsion comprises a combination of curcumin, demethoxycurcumin, and bisdemethoxycurcumin, which combination is solubilized in an oil phase having at least one polar oil with an HLB value of from about 0.7 to about 14, wherein the weight ratio of the bisdemethoxycurcumin to the curcumin is from about 1:1 to about 1:7 and the weight ratio of the bisdemethoxycurcumin to the demethoxycurcumin is from about 1:1 to about 1:2.5.

Yet another embodiment is directed to a method of making a nutritional composition comprising the steps of: (a) combining curcuminoids with a polar oil having an HLB of from about 0.7 to about 14, wherein said curcuminoids comprise curcumin, demethoxycurcumin, and bisdemethoxycurcumin; (b) heating the combination of curcuminoids and polar oil to a temperature sufficient to solubilize a fraction of the curcuminoids in the polar oil; and (c) removing an unsolubilized curcuminoid fraction from the heated combination to form a polar oil having an HLB of from about 0.7 to about 14 and comprising a weight ratio of solubilized bisdemethoxycurcumin to solubilized curcumin of from about 1:1 to about 1:7 and a weight ratio of bisdemethoxycurcumin to demethoxycurcumin of from about 1:1 to about 1:2.5; and then (d) formulating the combination of the polar oil and the solubilized curcuminoid fraction with fat, protein, and carbohydrate to form a nutritional composition.

It has now been found that curcuminoids can be selectively solubilized in oils having an HLB of from about 0.7 to about 14 (i.e., polar oils) so that the resulting distribution of solubilized curcuminoids in the oil is more bioactive and has better bioavailability than natural curcuminoid sources. Moreover, this new distribution of solubilized curcuminoids in polar oils has less impact on product color than natural curcuminoid distributions, i.e., increased bioactivity and or bioavailability per unit color. This new distribution is significantly different than that found in natural curcuminoid sources such as Turmeric which most typically contain a curcumin to demethoxycurcumin to bisdemethoxycurcumin weight ratio of approximately 10.7 to 2.6 to 1.

DETAILED DESCRIPTION OF THE INVENTION

The compositions and methods herein are directed to nutritional compositions comprising a shifted distribution of curcuminoids that have been solubilized in a polar oil having a defined HLB value. These and other essential or optional elements or features of the various embodiments are described in detail hereinafter.

The term "nutritional composition" means the referenced material comprises fat, protein, and carbohydrate and is suitable for oral administration to a human. The nutritional composition may further comprise vitamins, minerals and other ingredients and represent a sole, primary, or supplemental source of nutrition.

All percentages, parts and ratios as used herein are by weight of the total composition, unless otherwise specified. All such weights as they pertain to listed ingredients are based on the active level and, therefore, do not include solvents or by-products that may be included in commercially available materials, unless otherwise specified.

All numerical ranges as used herein, whether or not expressly preceded by the term "about", are intended and understood to be preceded by that term, unless otherwise specified.

The compositions and methods herein may also be free of any optional or other ingredient or feature described herein, provided that the remaining formula still contains the requisite ingredients or features as described herein. In this context, the term "free" means the selected composition or method contains or is directed to less than a functional amount of the ingredient or feature, typically less than 0.1% by weight, and also including zero percent by weight, of such ingredient or feature.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

Any reference to singular characteristics or limitations of the present disclosure shall include the corresponding plural characteristic or limitation, and vice versa, unless otherwise specified or clearly implied to the contrary by the context in which the reference is made.

Any combination of method or process steps as used herein may be performed in any order, unless otherwise specifically or clearly implied to the contrary by the context in which the referenced combination is made.

The nutritional compositions and methods may comprise, consist of, or consist essentially of the elements and features of the disclosure described herein, as well as any additional or optional ingredients, components, or features described herein or otherwise useful in a nutritional application.

Product Form

The nutritional compositions may be formulated and administered in any known or otherwise suitable oral form. Any solid, liquid, or powder form, including combinations or variations thereof, are suitable for use herein, provided such forms allow for safe and effective oral delivery to the individual of the essential ingredients as also defined herein.

The nutritional compositions are most suitably formulated as aqueous emulsions, including water-in-oil emulsions, oil-in-water emulsions, or complex (e.g., oil-in-water-in-oil emulsion) or other emulsion systems. As applied to the nutritional compositions herein, the nutritional emulsion embodiments are most typically oil-in-water emulsions comprising an internal or discontinuous oil phase that comprises the curcuminoids and polar oil components as described herein.

The emulsion embodiments include conventional emulsions having a mean a droplet diameter of greater than 0.8 microns, including greater than 1 micron, and also including from 1.2 microns to 5 microns.

Polar Oil

The nutritional compositions comprise a polar oil, which may represent all or some of the total fat in the compositions. The polar oil is defined by a selected HL B value that ultimately favors, along with the optional selection of proper processing temperatures, the dissolution of a beneficial ratio of individual curcuminoids as described herein.

HLB values are a well known measure of the degree to which a material is hydrophilic and or lipophilic, and may be determined by any one of a number of methods well known in the chemical or formulation arts. HLB values are often used to characterize the relative extent to which a surfactant, emulsifier or similar other material would favor solubility in oil or water. Materials having a higher HLB value would tend to favor solubility in water while materials having a lower HLB value would tend favor solubility in oil.

It has been found that curcuminoids can be dissolved in certain oils, the dissolution of which favors a more beneficial distribution or weight ratio of curcuminoids during typical processing temperatures. More specifically, it has been found that these certain oils (referred to herein as "polar oils") are those having HLB values within the ranges as described herein. Oils having HLB values below this range do not solubilize enough of the curcuminoids while oils having HLB values above this range more easily result in curcuminoid distributions outside the beneficial ranges (for curcuminoid ratios) during normal processing temperatures as defined herein.

It should be noted, however, that many of these polar oils can still be processed at temperatures sufficiently high to drive the curcuminoid distribution past the desirable curcuminoid distribution range and toward 100% dissolution of all of the curcuminoids. It is therefore not enough that the composition merely contains a combination of the polar oil and curcuminoids. Instead, the combination must also include the desired curcuminoid ratio as defined herein, which is most readily obtained by controlling and limiting processing temperatures during dissolution of the curcuminoid extract in the polar oil. It should also be noted that the recited curcuminoid distribution may be found in the nutritional composition or in an oil phase within of an emulsion embodiment hereof. For the latter, the nutritional emulsion may or may not contain an overall curcuminoid distribution within the ranges recited herein provided that it comprises an internal oil phase that does indeed contain selected curcuminoid distribution defined herein.

Polar oils suitable for use herein have an HLB value of from about 0.7 to about 14, including from about 1 to about 8, and also including from about 3 to about 7. It is understood that the selection of these oils, as well as any other nutrient described herein, must also be suitable for oral administration to be applicable to the present compositions.

Non limiting examples of suitable polar oils include medium chain triglyceride (MCT) oils. As used herein, the terms "medium chain triglyceride", "medium chain triglyceride oil" and "MCT oil" are used interchangeably and include triacylglycerol esters of C6-C12, more typically C6-10, fatty acids. The relative ratios of the different fatty esters can vary. The approximate ratios of these fatty acids in commercial MCT oils derived from coconut oil, for example, which are also suitable for use herein are 2(C6):55(C8):42 (C10):1(C12).

Other non-limiting examples of polar oils suitable for use in the compositions include C4-C18 fatty acids, C6-C18 monoglycerides, C8-C18 diglycerides, C4-C14 triglycerides, and mixtures or variations thereof. Another example of a suitable polar oil is Datem (diacetyl tartaric (acid) ester of monoglyceride). It is understood, however, that all such oils must also have the requisite HLB value to be effective for use as a polar oil herein.

The amount of the polar oil used in the nutritional composition varies depending upon a number of factors, including the desired amount of curcuminoids to be dissolved, the processing temperature employed during dissolution, and chemical nature of other ingredients in the composition. However, the polar oil most typically represents from about 0.1% to about 10%, including from about 0.3% to about 5%, by weight of the composition.

The polar oil may represent all or some of the fat in the composition, but will most typically represent from about 10% to 100%, including from about 20% to about 95%, and also including from about 50% to about 90%, by weight of the total fat or in the alternative by weight of the total fat in the oil phase of an oil-in-water emulsion embodiment.

Curcuminoids

The nutritional compositions comprise a combination of curcumin, demethoxycurcumin (DMC), and bisdemethoxycurcumin (BDMC) that are solubilized in selected ratios within the polar oil component, or an oil phase comprising the polar oil component, of the compositions.

The ratios of the individual curcuminoids in the nutritional compositions herein are different than the ratios found naturally in curcuminoid-containing plants and natural extracts. These new ratios designed to optimize their collective biological activity while minimizing their collective impact on the color of the nutritional composition. These new ratios include a weight ratio of bisdemethoxycurcumin to curcumin of more than about 1:8, including from about 1:1 to about 1:7, and also including from about 1:3 to about 1:7, and a weight ratio of bisdemethoxycurcumin to demethoxycurcumin of more than about 1:2.5, including from about 1:1 to about 1:2 including from about 1:1.5 to about 1:1.9.

The total curcuminoid concentration in the nutritional compositions may range from at least about 0.001%, including from about 0.002% to about 1.0%, including from about 0.005% to about 0.8%, also including from 0.03% to about 0.3%, and also including from about 0.1% to about 0.25%, by weight of the nutritional composition.

The term "total curcuminoid" as used herein means the amount or concentration of the combination of curcumin, demethoxycurcumin, and bisdemethoxycurcumin, excluding any other curcuminoids that may also be formulated into the composition.

Although the nutritional compositions may further comprise different types of curcuminoids, these compositions may also be free of such other types of curcuminoids. These compositions may also be free of unsolubilized curcuminoids, including unsolubilized curcumin, demethoxycurcumin, and bisdemethoxycurcumin.

The total curcuminoid concentration in the nutritional composition most suitably represents from about 50% to 100%, including from about 80% to about 98%, by weight of any and all curcuminoids in the compositions. In other words, it is desirable to have solubilized curcumin, solubilized demethoxycurcumin, and solubilized bisdemethoxycurcumin as the only curcuminoids in the nutritional compositions.

The three individual curcuminoids in the nutritional compositions have varying physical and biological activities, which activities are well known and reported in the literature. Curcumin, for example, has a higher natural distribution in Turmeric than in the nutritional compositions of the present disclosure. Curcumin also has a more intense yellow color as compared to demethoxycurcumin and bisdemethoxycurcumin as well as a lower metabolic recovery, inhibition of microtubule assembly, and uptake by colon cancer cells. bisdemethoxycurcumin by contrast provides higher metabolic recovery, inhibition of microtubule assembly, and uptake by colon cancer cells than either curcumin or demethoxycurcumin. Some of these know curcuminoids properties are summarized below.

| Property | Activity | | |
| --- | --- | --- | --- |
| | Curcumin | DMC | BDMC |
| Molecular Weight | 368.4 | 338.4 | 308.4 |
| Natural distribution in Turmeric, % w/w | 75% | 18% | 7% |
| Color (molar absorptivity) | 58,530 (428 nm) | 54,800 (424 nm) | 46,400 (416 nm) |
| Metabolic Recovery | ~50% | ~50% | ~75% |
| Inhibition of Microtubule Assembly | 50% @ 40 μm | 40% @ 30 μm | 70% @ 20 μm |
| Uptake by Colon Cancer Cells, relative to curcumin = 1.00 | 1.00 | 1.30 | 2.24 |
| Neuroprotective Activity, approximate | 1.00 | 0.50 | 0.00 |

The term "metabolic recovery" as used herein refers to the percentage of ingested curcuminoid actually metabolized by the body. The term "inhibition of microtubule assembly" as used herein refers to the ability to decrease the rate of cancer cell growth/procession by a curcuminoid. The term "cancer cell uptake" as used herein refers to the ability of the curcuminoid to enter into a cancer cell. These last two characteristics—inhibition of microtubule assembly and cancer cell uptake—are advantageous properties in that they may act to slow the progression of cancer cell growth.

In short, by optimizing the distribution or weight ratio of these individual curcuminoids as described herein, their biologically activities can be maximized while decreasing the intensity of undesirable yellow color imparted to the nutritional product.

Macronutrients

The nutritional compositions comprise fat, protein, and carbohydrate macronutrients. Any source of such nutrients that are known or otherwise suitable for use in an oral nutritional product is also suitable for use herein, provided that such nutrients are compatible with the selected ingredients in the composition and provided that the fat component includes the polar oil as described herein.

Although concentrations or amounts of each macronutrient in the compositions may vary depending upon the nutritional needs of the intended user, such concentrations or amounts most typically fall within one of the following embodied ranges A-F

| Macronutrient | Embodiment A | Embodiment B | Embodiment C |
| --- | --- | --- | --- |
| Carbohydrate % total calories | 10-70 | 20-60 | 40-60 |
| Protein % total calories | 10-65 | 10-50 | 15-35 |
| Fat % total calories | 5-40 | 10-30 | 15-25 |

| | Embodiment D | Embodiment E | Embodiment F |
| --- | --- | --- | --- |
| Carbohydrate wt/wt % | 1-40 | 4-30 | 10-20 |
| Protein wt/wt % | 0.1-30 | 0.5-15 | 1-5 |
| Fat wt/wt % | 0.5-30 | 1-15 | 2-10 |

The nutritional compositions comprise a fat source, which includes the polar oil component as described herein. The polar oil may represent all or just some of the fat source. Non-limiting examples of suitable fats for use in addition to the polar oils include coconut oil, fractionated coconut oil, soy oil, corn oil, olive oil, safflower oil, high oleic safflower oil, sunflower oil, high oleic sunflower oil, palm and palm kernel oils, palm olein, canola oil, marine oils, cottonseed oils, and combinations thereof. The term "fat" as used herein includes both fats and oils, solid or liquid, unless otherwise specified.

The nutritional compositions also comprise a carbohydrate source. Non limiting examples of suitable carbohydrates include hydrolyzed or modified starch or cornstarch, glucose polymers, corn syrup, corn syrup solids, rice-derived carbohydrate, glucose, fructose, lactose, high fructose corn syrup, indigestible oligosaccharides (e.g., fructooligosaccharides), honey, sugar alcohols (e.g., maltitol, erythritol, sorbitol), and combinations thereof.

The nutritional compositions also comprise a protein source. Non limiting examples of suitable protein sources include hydrolyzed, partially hydrolyzed or non-hydrolyzed proteins or protein sources, and can be derived from any known or otherwise suitable source such as milk (e.g., casein, whey), animal (e.g., meat, fish), cereal (e.g., rice, corn), vegetable (e.g., soy), or combinations thereof. Non-limiting examples of such proteins include milk protein isolates, casein protein isolates, milk protein concentrate, whole cows milk, partially or completely defatted milk, soy protein isolates, and so forth.

Optional Ingredients

The nutritional compositions may further comprise other optional components that may modify the physical, chemical, aesthetic or processing characteristics of the products or serve as pharmaceutical or additional nutritional components when used in a targeted population. Many such optional ingredients are known or otherwise suitable for use in nutritional products and may also be used in the compositions herein, provided that such optional ingredients are safe and effective for administration and are compatible with the essential and other selected components in the composition.

Non-limiting examples of such other optional ingredients include preservatives, anti-oxidants, buffers, pharmaceutical actives, sweeteners, colorants, flavors, flavor enhancers, thickening agents and stabilizers, emulsifying agents, lubricants, and so forth.

The nutritional compositions may further include one or more minerals, non-limiting examples of which include phosphorus, sodium, chloride, magnesium, manganese, iron, copper, zinc, iodine, calcium, potassium, chromium, molybdenum, selenium, and combinations thereof.

The nutritional compositions may also include one or more vitamins, non-limiting examples of which include carotenoids (e.g., beta-carotene, zeaxanthin, lutein, lycopene), biotin, choline, inositol, folic acid, pantothenic acid, choline, vitamin A, thiamine (vitamin B1), riboflavin (vitamin B2), niacin (vitamin B3), pyridoxine (vitamin B6), cyanocobalamin (vitamin B12), ascorbic acid (vitamin C), vitamin D, vitamin E, vitamin K, and various salts, esters or other derivatives thereof, and combinations thereof.

Method of Manufacture

The nutritional compositions may be prepared in accordance with the methods herein, or may be prepared by any known or otherwise suitable technique for bringing together the individual components, ingredients, and/or features into a finished nutritional product.

The methods for preparing the compositions may comprise the following steps:
(a) combining curcuminoids with a polar oil as defined herein, wherein the curcuminoids comprise curcumin, demethoxycurcumin (DMC), and bisdemethoxycurcumin (BDMC);
(b) heating the combination of curcuminoids and the polar oil to a temperature sufficient to solubilize a fraction but not all of the curcuminoids in the polar oil, wherein the resulting heated combination includes solubilized and unsolubilized curcuminoids;
(c) removing at least some, most typically from about 25% to 100% by, including from about 75% to about 100%, and also including from 80% to 95%, by weight of the unsolubilized curcuminoid fraction from the combination to form a solution comprising the polar oil and solubilized curcumin, solubilized demethoxycurcumin, and solubilized bisdemethoxycurcumin, within the weight ratios as defined herein; and
(d) introducing, adding, or otherwise formulating the solution comprising the polar oil and the solubilized curcuminoids into a nutritional composition as defined herein.

In accordance with step (a) of the method, the polar oil may be used alone or in combination with other oils. When used in combination with other oils, however, such combination must still be such that the combination during the method ultimately solubilizes at least a fraction of the curcuminoids to within the relative curcuminoid weight ratios as defined herein.

Also in accordance with step (a) of the method, and prior to heating of step (b), the resulting combination of curcuminoids and polar oil may comprise from about 0.25% to about 17%, including from about 0.4% to about 5%, also including from about 1.5% to about 3.5%, by weight of the curcuminoids.

Also in accordance with step (a), the combination of curcuminoids may be in the form of natural extracts from Turmeric or other natural curcuminoid sources, and thus may further comprise other curcuminoids other than curcumin, demethoxycurcumin, and bisdemethoxycurcumin.

In accordance with step (b) of the method, the combination of curcuminoids and polar oil are heated to a temperature and for a period of time sufficient to solubilize the desired fraction but not all of the curcuminoids. It is understood, however, that the polar oil may be heated before, during, or after addition of the curcuminoid source, so long as the heat provided allows for dissolution of the fraction of the curcuminoids. Oil temperatures may range up to about 90° C., including from about 20° C. to about 75° C., also including from about 40° C. to about 65° C. Oil temperatures of about 55° C. are highly effective.

The distribution (i.e. relative weight ratios) of the individual solubilized curcuminoids within the soluble fraction can be further modified by adjusting the temperature of the polar oil in step (b). In other words, because of the different solubility profiles of curcumin, demethoxycurcumin, and bisdemethoxycurcumin in the polar oil, the temperature in step (b) may be selected to modify and help achieve the desired ratio of the solubilized curcuminoids in the polar oil. Curcumin, for example, which is the major curcuminoid in the compositions, is not appreciably soluble in MCT oil at temperatures below 95° C., however, it is now predicted that complete curcuminoid solubility will be achieved in the polar oil, especially when the polar oil comprises MCT oil, at about 163° C.

The highest efficiency (i.e., property or activity per unit color) for desirable properties of the nutritional composition, such as metabolic recovery, inhibition of microtubule protein assembly, and uptake by cancer cells, is achieved at about 55° C., which allows for the greatest enrichment of bisdemethoxycurcumin in the nutritional composition. Accordingly, a balance is made between optimal solubility and efficiency of the curcuminoids in the end nutritional composition to determine the temperature at which the combination of curcuminoids and polar oil are heated in the method herein.

In accordance with step (c) of the method, once the combination of curcuminoids and polar oil are sufficiently heated and solubilized, the unsolubilized curcuminoid fraction from the combination is removed or otherwise separated from the polar oil composition. The unsolubilized fraction may be removed or separated from the polar oil composition using any known or otherwise suitable technique for removing unsolubilized solids from oil. For example, the unsolubilized fraction can be removed using centrifugation or filtration. More particularly, in one embodiment, the unsolubilized fraction may be removed using a thermostatted centrifuge, which has temperature control capability in that it is capable of maintaining a temperature of from about 15° C. to about 90° C.

The methods may further include formulating the solubilized curcuminoid fraction into a nutritional composition comprising fat, protein, and carbohydrate. This may be achieved by any known or otherwise suitable method for adding a fat to a nutritional composition, including a nutritional aqueous emulsion. Once the ingredients are combined, they are often transferred to a suitable device and homogenized to form a stable oil-in-water emulsion The above method may include any one or more of the other formulation or other feature described herein for the nutritional compositions.

EXAMPLES

The following examples illustrate specific embodiments and or features of the nutritional compositions and or methods. The examples are given solely for the purpose of illustration and are not to be construed as limitations, as many variations thereof are possible without departing from the spirit and scope of the invention.

Example 1

A suspension is prepared comprising 2.4% by weight of CURCUMIN C3 COMPLEX® (Sabinsa Corporation, Payson, Utah) in NEOBEE® 1053 (MCT oil from Stepan Company, Northfield, Ill.). The suspension is heated to temperatures of from 55° C. to 165° C., during which the temperature is maintained for about two minutes at each of 55° C., 65° C., 75° C., 85° C., 95° C., and 165° C. An aliquot is taken from the suspension during each of the two minute temperature plateaus and centrifuged five minutes at 15,000×g to thus remove undissolved solids from the suspension. The centrifuged aliquot, which is now a solution comprising solubilized curcuminoids, is diluted in a 2:100 volume ratio with dimethylsulfoxide and tested for curcuminoid content using high pressure liquid chromatography (HPLC). The results are summarized below.

|   | Temp. C.° | Soluble curcuminoids, % of total curcuminoids | Soluble curcumin, as % of total curcumin | Soluble DMC, as % of total DMC | Soluble BDMC, as % of total BDMC | BDMC to DMC wt ratio | BDMC to curcumin wt ratio |
|---|---|---|---|---|---|---|---|
| A | 22[1] | 17.4 | 7.7 | 38.1 | 80.1 | 1:1.6 | 1:1.2 |
| B | 55 | 19.4% | 9.5% | 40.7% | 84.8% | 1:1.6 | 1:1.4 |
| C | 65 | 22.9% | 11.2% | 49.7% | 89.4% | 1:1.8 | 1:1.6 |
| D | 75 | 27.0% | 14.0% | 57.9% | 94.9% | 1:2.0 | 1:1.9 |
| E | 85 | 32.3% | 18.6% | 65.8% | 99.4% | 1:2.2 | 1:2.3 |
| F | 95 | 38.6% | 25.5% | 70.8% | 100.6% | 1:2.3 | 1:3.2 |
| G | 165 | 100% | 100% | 100% | 100% | 1:2.6 | 1:10.7 |
| CC3 Powder[2] | — | — | — | — | — | 1:2.6 | 1:10.7 |

[1]Room temperature
[2]CURCUMIN C3 COMPLEX Powder not combined with MCT oil

The above table illustrates the extent to which the curcuminoid ratios in CURCUMIN C3 COMPLEX® shift when combined with oil having an HLB value of between 0.7 and 11 (e.g., MCT oil with HLB value of 1.4) as a function of oil temperature. Aliquots F and G solubilized the curcuminoids to outside the beneficial ranges defined herein. Each of the resulting Aliquots A-E, however, fall within the requisite curcuminoid ratios, and thus provide increased bioactivity and bioavailability due to a solubility shift that favors an increase in the relative amount of BDMC to DMC and BDMC to curcumin. At the same time, each of the resulting solutions A-E also have a reduced color impact (i.e., increased bioactivity per unit color) due to a solubility shift that favors the less colorful BDMC. Optimal curcuminoid ratios for bioactivity, bioavailability and color impact occur at about 55° C.

Example 2-5

Examples 2-5 illustrate nutritional compositions of the present disclosure formulated as oil-in-water emulsions. The ingredients for each exemplified composition are described in the following tables. All ingredient amounts are listed as kg per 1000 kg batch of product, unless otherwise specified.

| Ingredient | Example 2 | Example 3 | Example 4 | Example 5 |
| --- | --- | --- | --- | --- |
| Water | QS | QS | QS | QS |
| Corn maltodextrin | 118.18 | 118.18 | 118.18 | 118.18 |
| Sodium caseinate | 34.19 | 34.19 | 34.19 | 34.19 |
| Milk protein isolate | 31.37 | 31.37 | 31.37 | 31.37 |
| Sucrose | 26.39 | 26.39 | 26.39 | 26.39 |
| Corn syrup | 16.93 | 16.93 | 16.93 | 16.93 |
| Sardine oil | 15.35 | 15.35 | 15.35 | 15.35 |
| Fructooligosaccharide (FOS) | 13.16 | 13.16 | 13.16 | 13.16 |
| NEOBEE® 1053[1] | 11.76 | 11.76 | 11.76 | 11.76 |
| Calcium caseinate | 9.337 | 9.337 | 9.337 | 9.337 |
| Sodium citrate | 3.378 | 3.378 | 3.378 | 3.378 |
| Potassium citrate | 3.372 | 3.372 | 3.372 | 3.372 |
| Canola oil | 3.265 | 3.265 | 3.265 | 3.265 |
| Magnesium chloride | 2.678 | 2.678 | 2.678 | 2.678 |
| Micronized tri-calcium phosphate MTCP | 2.183 | 2.183 | 2.183 | 2.183 |
| Soybean oil | 1.932 | 1.932 | 1.932 | 1.932 |
| Flavor | 1.800 | 1.800 | 1.800 | 1.800 |
| Curcuminoids (extracted at 22° C.) | 0.100 | | | |
| Curcuminoids (extracted at 55° C.) | | 0.500 | | |
| Curcuminoids (extracted at 65° C.) | | | 0.750 | |
| Curcuminoids (extracted at 75° C.) | | | | 2.000 |
| Lecithin | 1.380 | 1.380 | 1.380 | 1.380 |
| Magnesium phosphate dibasic | 0.5860 | 0.5860 | 0.5860 | 0.5860 |
| Choline chloride | 0.5511 | 0.5511 | 0.5511 | 0.5511 |
| Potassium hydroxide 45% solution | 0.2862 | 0.2862 | 0.2862 | 0.2862 |
| Ascorbic acid | 0.2650 | 0.2650 | 0.2650 | 0.2650 |
| Taurine | 0.2646 | 0.2646 | 0.2646 | 0.2646 |
| Water soluble premix | 0.2510 | 0.2510 | 0.2510 | 0.2510 |
| Potassium chloride | 0.1596 | 0.1596 | 0.1596 | 0.1596 |
| L-Carnitine | 0.1500 | 0.1500 | 0.1500 | 0.1500 |
| Trace/Ultra Trace Minerals | 0.1317 | 0.1317 | 0.1317 | 0.1317 |
| Vitamins D, E, K | 0.0956 | 0.0956 | 0.0956 | 0.0956 |
| Ascorbyl palmitate | 0.064 | 0.064 | 0.064 | 0.064 |
| Carrageenan | 0.0611 | 0.0611 | 0.0611 | 0.0611 |
| Vitamin A palmitate | 0.0165 | 0.0165 | 0.0165 | 0.0165 |
| Tocopherol-2 Antioxidant | 0.011 | 0.011 | 0.011 | 0.011 |
| Potassium iodide | 0.0002 | 0.0002 | 0.0002 | 0.0002 |

[1]MCT oil from Stepan Company, Northfield, Illinois

The curcuminoid blends for use in the illustrated examples comprise solubilized curcumin, demethoxycurcumin (DMC), and bisdemethoxycurcumin (BDMC), and are free of undissolved curcuminoids.

The curcuminoid blends are prepared by first combining CURCUMIN C3 COMPLEX® (Sabinsa Corporation, Payson, Utah) in powder form with a polar oil (NEOBEE® 1053). The initial combination comprises between 0.25% and 17% by weight of the CURCUMIN C3 COMPLEX. The initial combination is then heated to the desired temperature (22° C., 55° C., 65° C., or 75° C.) to solubilize a fraction of the curcuminoids in the polar oil, wherein the resulting heated combination includes solubilized and unsolubilized curcuminoids. The undissolved curcuminoids or solids are then removed from the heated combination by centrifugation to form from the combination a solution comprising the polar oil and solubilized curcumin, solubilized demethoxycurcumin, and solubilized bisdemethoxycurcumin, wherein the weight ratio of the solubilized bisdemethoxycurcumin to solubilized demethoxycurcumin is between 1:1 and 1:2.5 and the weight ratio of solubilized bisdemethoxycurcumin to curcumin is between 1:1 and 1:7. Each of the curcuminoid blends used in Examples 2-5 have the BDMC to DMC and BDMC to curcumin ratios as those described for the corresponding Example 1 aliquots described in Example 1

Each of the nutritional emulsions described in Examples 2-5 may be prepared in accordance with the methods described herein. Generally, once the curcuminoid blend is prepared (as above), it and the other ingredients may be formulated into the desired nutritional by forming at least three separate slurries (carbohydrate-mineral slurry, protein slurry, fat slurry including the above curcuminoid blends) as appropriate for the different ingredients, and then blend the various slurries together, heat treat and homogenize the resulting blend, and then standardize. The resulting composition is then flavored, aseptically packaged into bottles or retort sterilized The resulting nutritional emulsions are oil-in-water emulsions having minimal color impact from the curcuminoid blend.

What is claimed is:

1. A method of making a nutritional composition comprising the steps of:
   (a) combining curcuminoids with a polar oil having an HLB of from about 0.7 to about 14, wherein said curcuminoids comprise curcumin, demethoxycurcumin, and bisdemethoxycurcumin;
   (b) heating the combination of curcuminoids and polar oil to a temperature sufficient to solubilize a fraction of the curcuminoids in the polar oil; and
   (c) removing an unsolubilized curcuminoid fraction from the heated combination to form a polar oil comprising a weight ratio of solubilized bisdemethoxycurcumin to solubilized curcumin of from about 1:1 to about 1:7 and a weight ratio of solubilized bisdemethoxycurcumin to solubilized demethoxycurcumin of from about 1:1 to about 1:2.5; and then
   (d) formulating the combination of the polar oil and the solubilized curcuminoid fraction with fat, protein, and carbohydrate to form a nutritional composition.

2. The method of claim 1 wherein the combination of curcuminoids and polar oil is heated to a temperature of from about 20° C. to about 90° C.

3. The method of claim 1 wherein the combination of curcuminoids and polar oil is heated to a temperature of from about 40° C. to about 65° C.

4. The method of claim 1 wherein the polar oil has an HLB of from about 1 to about 8.

5. The method of claim 1 wherein the polar oil is a medium chain triglyceride oil.

6. The method of claim 1 wherein the combination of curcuminoids and polar oil comprises from about 0.4% to about 17% by weight of the curcuminoids.

7. The method of claim 1 wherein the polar oil has an HLB value of from about 1 to about 8 and represents from about 10% to 100% by weight of the fat in the composition.

8. The method of claim 1 wherein the composition comprises from about 0.1% to about 5% by weight of medium chain triglyceride oil.

9. The method of claim 1 wherein the weight ratio of the bisdemethoxycurcumin to the curcumin is from about 1:3 to about 1:7.

10. The method of claim 1 wherein the weight ratio of the bisdemethoxycurcumin to the demethoxycurcumin is from about 1:1 to about 1:2.0.

* * * * *